US008194911B2

(12) United States Patent
Dyer et al.

(10) Patent No.: US 8,194,911 B2

(45) **Date of Patent: *Jun. 5, 2012**

(54) EARPHONE INTEGRATED EARTIP

(75) Inventors: Medford Alan Dyer, San Diego, CA (US); Simon Andre Sollberger, Laguna Beach, CA (US)

(73) Assignee: Logitech International, S.A. (CH)

(*) Notice: Subject to any disclaimer, the term of this patent is extended or adjusted under 35 U.S.C. 154(b) by 1262 days.

This patent is subject to a terminal disclaimer.

(21) Appl. No.: 11/728,733

(22) Filed: Mar. 27, 2007

(65) Prior Publication Data

US 2008/0240485 A1 Oct. 2, 2008

(51) Int. Cl.
*H04R 25/00* (2006.01)
*A61B 7/02* (2006.01)

(52) U.S. Cl. ......... 381/382; 381/380; 381/182; 181/135

(58) Field of Classification Search .................. 181/130, 181/135; 381/182, 309, 322, 380, 382, 395; D14/205, 223

See application file for complete search history.

(56) References Cited

U.S. PATENT DOCUMENTS 5,068,901 A 11/1991 Carlson
5,659,156 A 8/1997 Mauney et al.
5,692,059 A * 11/1997 Kruger .......................... 381/151
6,122,388 A 9/2000 Feldman
D478,991 S 8/2003 Dyer et al.
6,688,421 B2 2/2004 Dyer et al.
2006/0133630 A1* 6/2006 Harvey ......................... 381/312
2006/0133636 A1* 6/2006 Harvey et al. ................. 381/380
2007/0053540 A1* 3/2007 Harvey ......................... 381/380

OTHER PUBLICATIONS

Jabra MiniGels, http://www.jabra.com/JabraCMS/NA/EN/MainMenu/Products/Accessories/JabraMiniGels/Jabraminigels, Mar. 27, 2007, p. 1.

Jabra EarGels, http://www.jabra.com/JabraCMS/NA/EN/MainMenu/Products/Accessories/JabraEarGels/, Mar. 27, 2007, p. 1.

Comply Whoomp! Earbud Enhancer, http://www.hearingcomponents.com/cgi-bin/shopper.cgi?search=action&category=0141&keywords=all, Mar. 27, 2007, pp. 1-3.

* cited by examiner

*Primary Examiner* — Jesse Elbin

(74) *Attorney, Agent, or Firm* — Patent Law Office of David G. Beck

(57) ABSTRACT

An integrated eartip (501) that utilizes a one-piece, rather than a multi-piece, design is provided. The one-piece design is comprised of a first portion that includes at least one, or at least two, sound delivery tubes (513/515) and a second portion that is comprised of a compressible region. The integrated eartip also includes means for releasably attaching the eartip to an earphone in general, and a coupling member (503) in particular, thus allowing the eartip to be replaced as desired. When attached, the sound delivery tube, or tubes, of the integrated eartip are aligned with the acoustic port, or ports, of the earphone/coupling member. The first and second portions of the integrated eartip may exhibit different rigidity and/or compressibility characteristics. The integrated eartip can be fabricated from a single material such as a natural or synthetic elastomer.

22 Claims, 12 Drawing Sheets

801

EARPHONE INTEGRATED EARTIP

FIELD OF THE INVENTION

The present invention relates generally to audio monitors and, more particularly, to an earphone eartip.

BACKGROUND OF THE INVENTION

Earphones, also referred to as in-ear monitors, canal phones and earpieces, are commonly used to listen to both recorded and live music. A typical recorded music application would involve plugging the earphone into a music player such as a CD player, flash or hard drive based MP3 player, home stereo, or similar device using the earphone's headphone jack. Alternately, the earphone can be wirelessly coupled to the music player. In a typical live music application, an on-stage musician wears the earphone in order to hear his or her own music during a performance.

Earphones are typically quite small and are worn just outside the ear canal. Prior art earphones use either one or more diaphragm-based drivers, one or more armature-based drivers, or a combination of both driver types. Broadly characterized, a diaphragm is a moving-coil speaker with a paper or mylar diaphragm. Since the cost to manufacture diaphragms is relatively low, they are widely used in many common audio products. In contrast to the diaphragm approach, an armature receiver utilizes a piston design. Due to the inherent cost of armature receivers, however, they are typically only found in hearing aids and high-end in-ear monitors.

Armature drivers, also referred to as balanced armatures, were originally developed by the hearing aid industry. This type of driver uses a magnetically balanced shaft or armature within a small, typically rectangular, enclosure. A single armature is capable of accurately reproducing low-frequency audio or high-frequency audio, but incapable of providing high-fidelity performance across all frequencies. To overcome this limitation, armature-based earphones often use two, or even three, armature drivers. In such multiple armature arrangements, a crossover network is used to divide the frequency spectrum into multiple regions, i.e., low and high or low, medium, and high. Separate armature drivers are then used for each region, individual armature drivers being optimized for each region. In contrast to the multi-driver approach often used with armature drivers, earpieces utilizing diaphragm drivers are typically limited to a single diaphragm due to the size of the diaphragm assembly. Unfortunately, as diaphragm-based monitors have significant frequency roll off above 4 kHz, an earpiece with a single diaphragm cannot achieve the desired upper frequency response while still providing an accurate low frequency response.

In addition to utilizing one or more high-fidelity drivers, professional-quality earphones are either custom molded or they use generic eartips, also referred to as sleeves. For a custom molded earphone, a mold is first taken of the intended user's ear canal for a single earphone, or both ear canals for a pair of earphones. The custom earphones are then constructed by positioning some or all of the audio components within the earphone shells, the shells being fabricated from the molds taken of the user's ear canals. As the outside of the earphone shell is designed to exactly complement the inside of the user's ear canals, such earphones are typically very comfortable. Generic eartips offer a less expensive alternative to custom molded earphones. Such eartips use soft, pliable materials such as foam or silicon to provide a snug, comfortable fit at a fraction of the cost of a custom molded earphone. In use, both generic eartips and custom molded earphones attempt to isolate the user by minimizing audio interference caused by competing background noise.

Although many users find that generic eartips provide a comfortable fit, some users, typically those with smaller ear canals, still find that even the smallest available eartips are too large to fit comfortably within their ears. Accordingly, what is needed in the art is an easily replaceable generic eartip that can be sized to fit a wide range of users. The present invention provides such an eartip.

SUMMARY OF THE INVENTION

The present invention provides an integrated eartip that utilizes a one-piece, rather than a multi-piece, design. The one-piece design is comprised of a first portion that includes at least one, or at least two, sound delivery tubes and a second portion that is comprised of a compressible region. The integrated eartip of the invention also includes means for releasably attaching the eartip to an earphone in general, and a coupling member in particular, thus allowing the eartip to be replaced as desired. When attached, the sound delivery tube, or tubes, of the integrated eartip are aligned with the acoustic port, or ports, of the earphone/coupling member. The first and second portions of the integrated eartip may exhibit different rigidity and/or compressibility characteristics. The integrated eartip can be fabricated from a single material such as a natural or synthetic elastomer.

In one embodiment, an earphone is provided that is comprised of a coupling member, an earphone enclosure, signal receiving means, at least a pair of drivers disposed within the earphone enclosure, and an integrated eartip, the integrated eartip utilizing a one-piece design comprised of a first portion that includes at least a pair of sound delivery tubes and a second portion comprised of a compressible region. When attached, the sound delivery tubes of the integrated eartip are aligned with the acoustic ports of the earphone/coupling member. The signal receiving means can be comprised of a source input cable coupleable to an external source (e.g., music players, mixers, headphone amplifiers, etc.) and a circuit, the circuit being coupled to the source input cable and providing input signals to the drivers. The earphone enclosure and coupling member can be incorporated into a single component. The first and second portions of the integrated eartip may exhibit different rigidity and/or compressibility characteristics. The integrated eartip can be fabricated from a single material such as a natural or synthetic elastomer.

A further understanding of the nature and advantages of the present invention may be realized by reference to the remaining portions of the specification and the drawings.

DESCRIPTION OF THE SPECIFIC EMBODIMENTS

Figure 1:
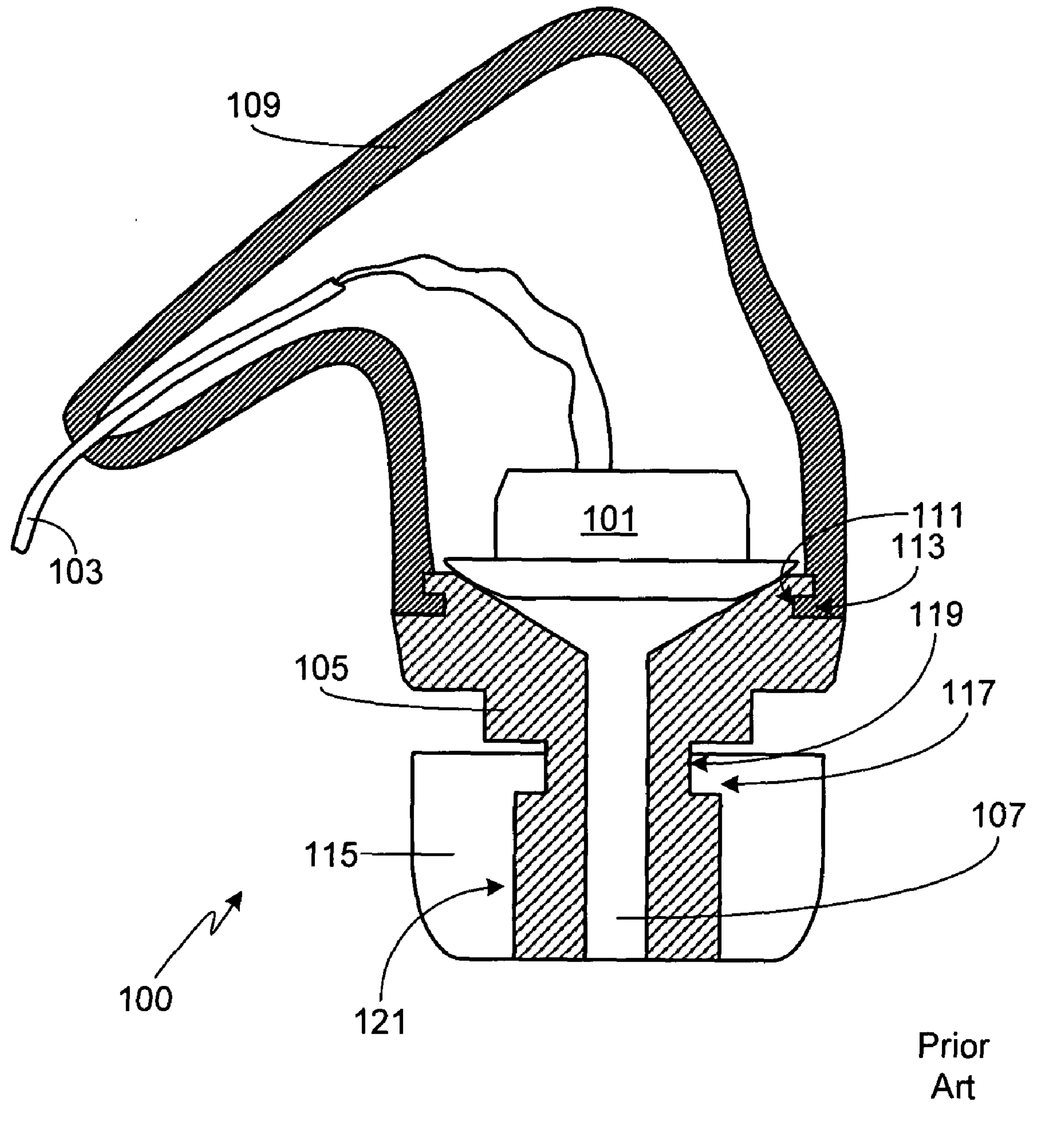
FIG. 1 is a cross-sectional view of a generic earphone with a single diaphragm driver in accordance with the prior art.

FIG. 1 is a cross-sectional view of a generic earphone 100 in accordance with the prior art. Earphone 100, also referred to herein as an earpiece, in-ear monitor and canalphone, includes a single diaphragm driver 101. Driver 101 is coupled to the external sound source (not shown) via a cable 103. Only a portion of cable 103 is shown. The external sound source may be selected from any of a variety of sources such as an audio receiver, mixer, music player, headphone amplifier or other source type. As is well known in the industry, earphone 100 can also be wirelessly coupled to the desired source.

As illustrated, the output from driver 101 is acoustically coupled to sound delivery member 105, member 105 including a sound delivery tube 107 that delivers the audio from driver 101 to the user. Sound delivery member 105 is designed to fit within the outer ear canal of the user and as such, is generally cylindrical in shape.

An outer earphone enclosure 109 attaches to sound delivery member 105. Earphone enclosure 109 protects the driver from damage while providing a convenient means of securing cable 103, or a cable socket, to the earphone. Enclosure 109 can be attached to member 105 using interlocking members (e.g., groove 111, lip 113). Alternately, an adhesive or other means can be used to attach enclosure 109 to member 105. Enclosure 109 can be fabricated from any of a variety of materials, thus allowing the designer and/or user to select the material’s firmness (i.e., hard to soft), texture, color, etc.

Attached to the end portion of sound delivery member 105 is an eartip 115, also referred to as an eartip sleeve or simply a sleeve. Eartip 115 can be fabricated from any of a variety of materials including foam, plastic and silicon-based material. Sleeve 115 can have the generally cylindrical and smooth shape shown in FIG. 1, or can include one or more flanges. To hold sleeve 115 onto member 105 during normal use, but still allow the sleeve to be replaced when desired, typically the eartip includes a lip portion 117 which is fit into a corresponding channel or groove 119 in sound delivery member 105. The combination of an interlocking groove 119 with a lip 117 provides a convenient means of replacing eartip 115, allowing sleeves of various sizes, shapes, or colors to be easily attached to the earphone. As a result, it is easy to provide the end user with a comfortable fit at a fraction of the cost of a custom fit (i.e., molded) earphone. Additionally, the use of interlocking members 117 and 119 allow worn out eartips to be quickly and easily replaced. It will be appreciated that other eartip mounting methods can be used with earphone

100. For example, eartip 115 can be attached to sound delivery member 105 using pressure fittings, bonding, etc.

Figure 2:
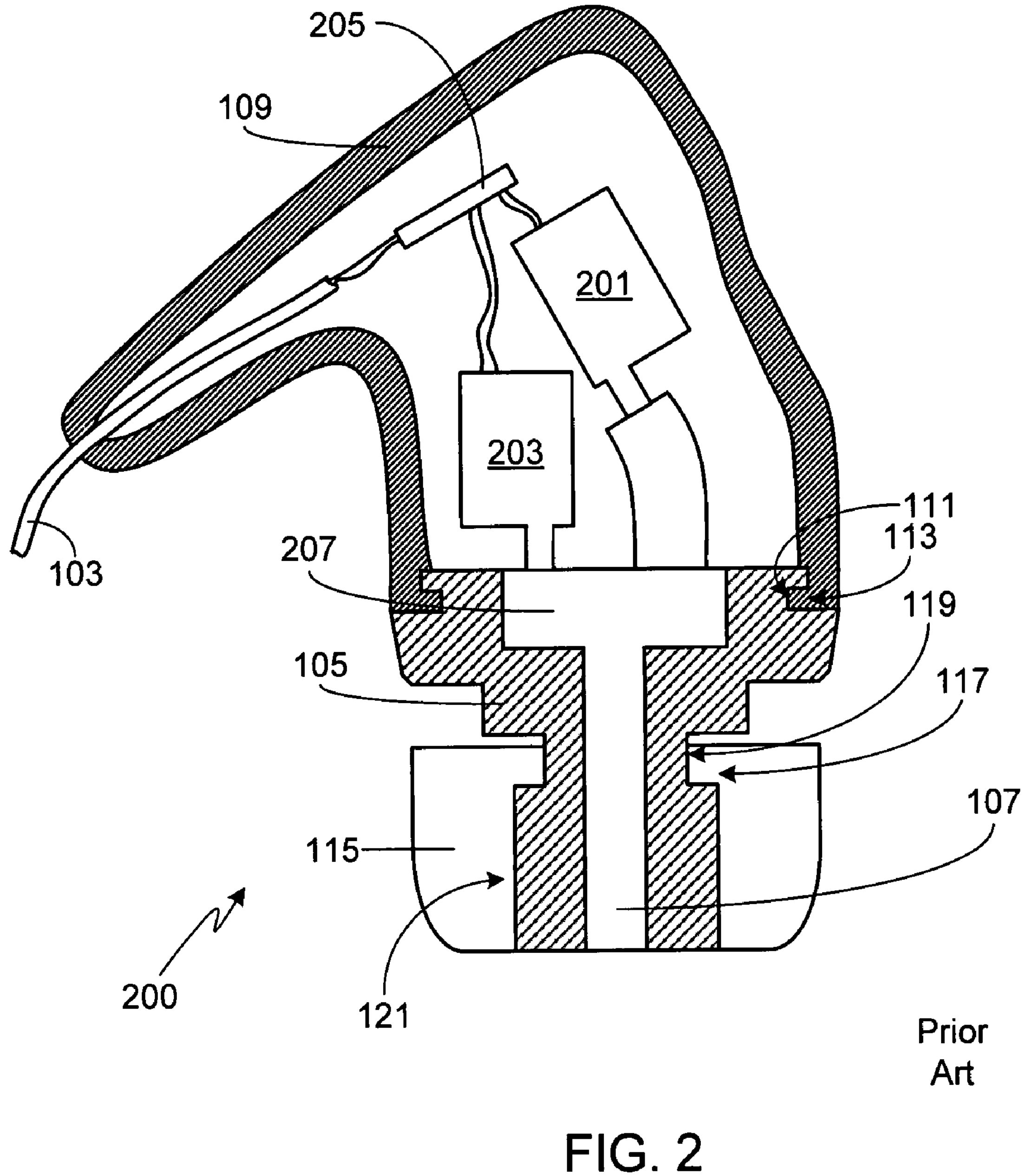
FIG. 2 is a cross-sectional view of a generic earphone with dual armature drivers in accordance with the prior art.

The use of a replaceable eartip is not limited to diaphragm-based earphones or earphones that use a single driver. For example, FIG. 2 is a cross-sectional view of a generic earphone 200 in accordance with the prior art which includes both a low-frequency armature driver 201 and a high-frequency armature driver 203. A circuit 205, such as a passive crossover circuit or an active crossover circuit, provides input to armature drivers 201 and 203. Crossover circuit 205 is coupled to the external sound source via cable 103. As illustrated, the output from each driver enters an acoustic mixing chamber 207 within sound delivery member 105. As in the previous earphone, a single sound delivery tube 107 delivers the audio to the user, in this example the audio being the mixed audio from the two drivers.

Figure 3:
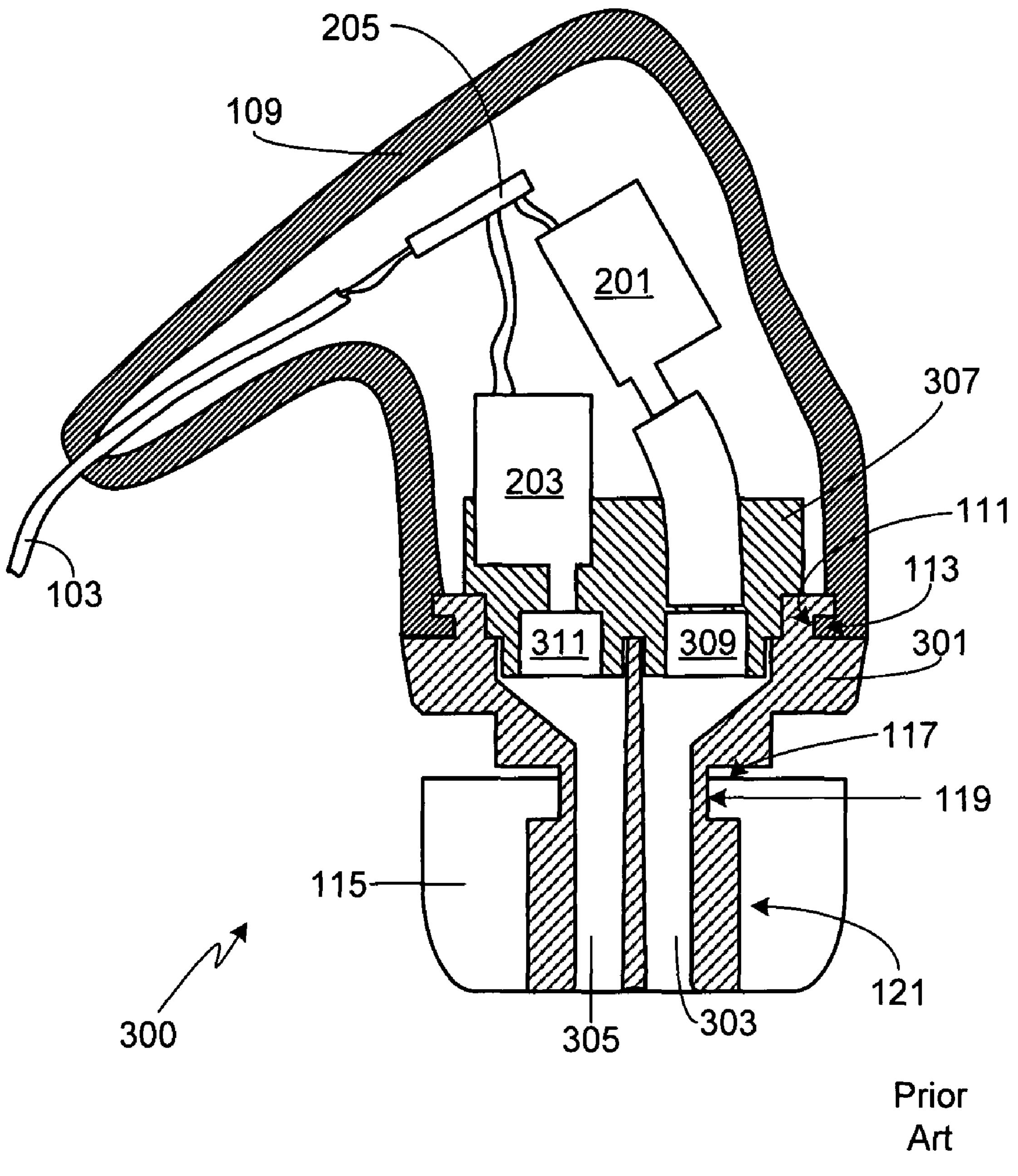
FIG. 3 is a cross-sectional view of a generic earphone with multiple sound delivery tubes in accordance with the prior art.

It will be appreciated that although a single sound delivery tube 107 is shown in the earphone illustrated in FIG. 2, multiple sound delivery tubes can be used as illustrated in FIG. 3. As shown, sound delivery member 301 of earphone 300 includes two separate sound delivery tubes 303/305, corresponding to drivers 201 and 203, respectively. Preferably a boot member 307, which can also be used in other configurations such as those shown in FIGS. 1 and 2, attaches to sound delivery member 301, boot member 307 securing the components to the sound delivery member.

Regardless of the configuration, earphones often utilize internal dampers, also commonly referred to as acoustic filters. Although not shown in FIGS. 1 or 2, the earphone illustrated in FIG. 3 includes a pair of dampers 309/311 interposed between the drivers 201/203 and sound delivery tubes 303/305. In the earphone illustrated in FIG. 2, the damper could be located within the mixing chamber 207, for example. Dampers, interposed between the driver(s) and the sound delivery tube(s) and/or the sound delivery tube(s) and the earphone output, are often used to tune the earphone, for example by reducing the output level for a particular frequency range or reducing the overall sound pressure level.

Figure 4:
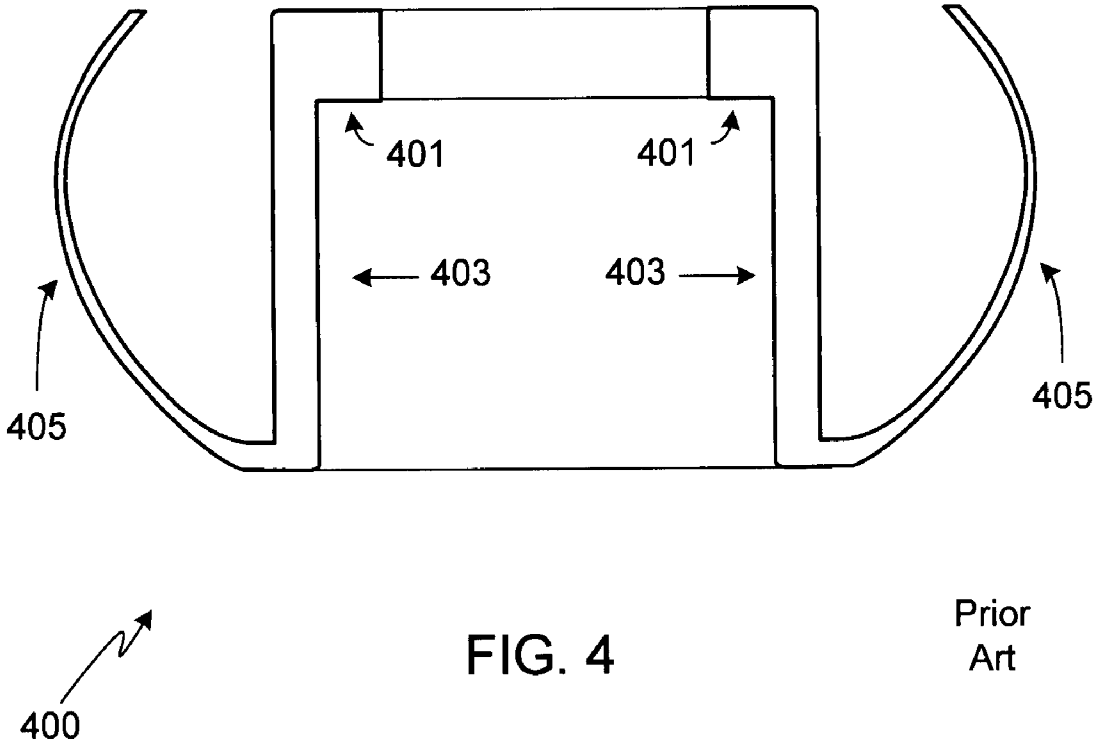
FIG. 4 Prior Art
FIG. 4 is a cross-sectional view of an alternate prior art eartip in accordance with the prior art.

Although eartip 115, as illustrated in the cross-sectional views of FIGS. 1-3, is solid, it will be appreciated that other configurations can be used. For example, FIG. 4 is a cross-sectional view of an alternate eartip 400. As shown, preferably eartip 400 includes a lip portion 401, thus allowing it to be easily attached to the sound delivery member groove as previously described and illustrated relative to eartip 115. Portion 403 of eartip 400 is cylindrically-shaped, thus providing a secure fit against the barrel-shaped region of the sound delivery member (e.g., region 121 of members 105 and 301). Eartip 400 also includes a pliable flanged portion 405 designed to provide a tight and comfortable fit within the user’s ear canal.

As illustrated in FIGS. 1-4, the prior art removable eartips fit over a barrel-shaped region of the sound delivery member. The barrel-shaped region of the sound delivery member, typically fabricated from a hard plastic, must be large enough to accommodate the sound delivery tubes, a difficult requirement if the earpiece uses multiple sound delivery tubes as in the earphone shown in FIG. 3. Additionally, the barrel-shaped region must provide the necessary support for the eartip as well as a means of mounting the eartip (e.g., groove 119). In addition to the sound delivery member, the diameter of the portion of the earphone that fits within the user’s ear is also governed by the thickness of the eartip itself. For the eartip shown in FIGS. 1-3, this thickness is due to the size of the eartip walls and the compressibility of the material comprising the eartip. For the eartip shown in FIG. 4, this thickness is due to the dimensions of portions 403 and 405, as well as the compressibility of the eartip material. Accordingly, the structural limitations of a conventional earphone, specifically the dimensions and compressibility of the sound delivery member and the eartip, limit the range of users that can achieve a comfortable fit using such an earphone.

Figure 5:
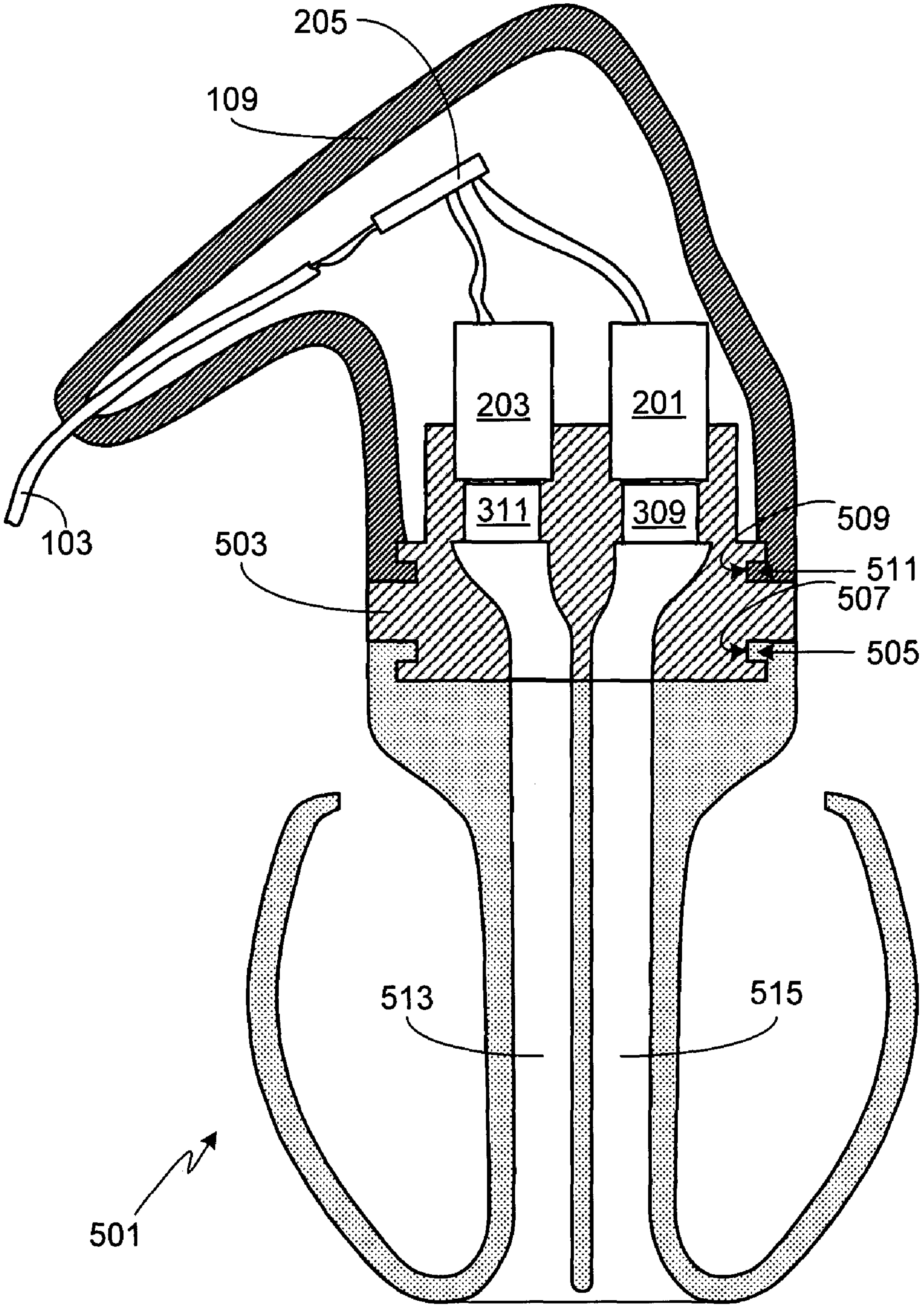
FIG. 5 is a cross-sectional view of an earphone using an integrated eartip in accordance with the invention.

FIG. 5 illustrates a preferred embodiment of the invention. As shown, the earphone uses an integrated eartip 501, the integrated eartip combining the functionality of the barrel-shaped region 121 of a conventional sound delivery member with a conventional eartip into a one-piece design. As such, integrated eartip 501 is capable of achieving a smaller diameter than the prior art approach, thus allowing integrated eartip 501 to comfortably fit within smaller ear canals. Additionally, depending upon the rigidity of the material used to fabricate the integrated eartip, the eartip design of the invention also allows the integrated eartip to be bent relative to the body of the earphone, thereby further increasing the chances of the end user obtaining a comfortable fit. Note that due to the rigidity of the barrel-shaped region 121 of a conventional sound delivery member, the eartip of a conventional earphone is not allowed to bend relative to the earphone body.

It will be appreciated that the invention, i.e., an integrated eartip, can be coupled to an earphone in a variety of ways and that the invention is not limited to one method in particular. In the preferred embodiment, integrated eartip 501 is coupled to the earphone in general, and to a coupling member 503 in particular, by a temporary means, thus allowing the integrated eartip to be easily replaced, for example with an integrated eartip of a different size. Preferably integrated eartip 501 includes a lip portion 505 which fits within a corresponding channel or groove 507 in coupling member 503 when the two components are coupled together. It will be appreciated that other eartip mounting methods can be used to couple the integrated eartip to the earphone, for example pressure fittings or semi-permanent adhesives.

In the preferred embodiment shown in FIG. 5, outer earphone enclosure 109 attaches directly to coupling member 503, for example using interlocking members (e.g., groove 509, lip 511). Alternately, and as described relative to the prior art, an adhesive or other means can be used to attach enclosure 109 to coupling member 503.

Figures 6, 7:
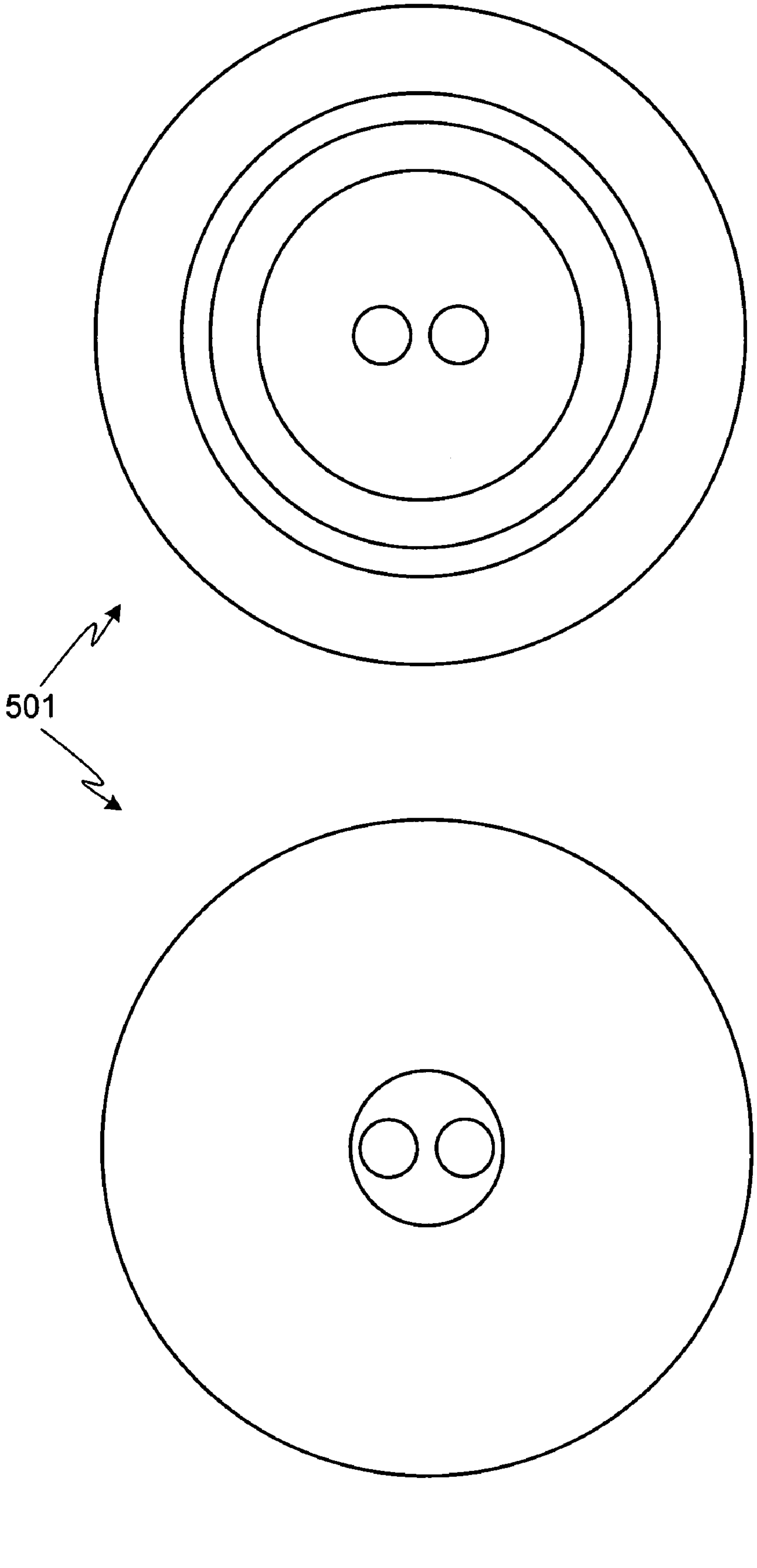
FIG. 6 is an end view of the integrated eartip shown in FIG. 5 from the input side.
FIG. 7 is an end view of the integrated eartip shown in FIG. 5 from the output side.

For purposes of clarity, FIG. 6 is an end-view of integrated eartip 501 from the input side while FIG. 7 is an end-view of integrated eartip 501 from the output side.

Figure 8:
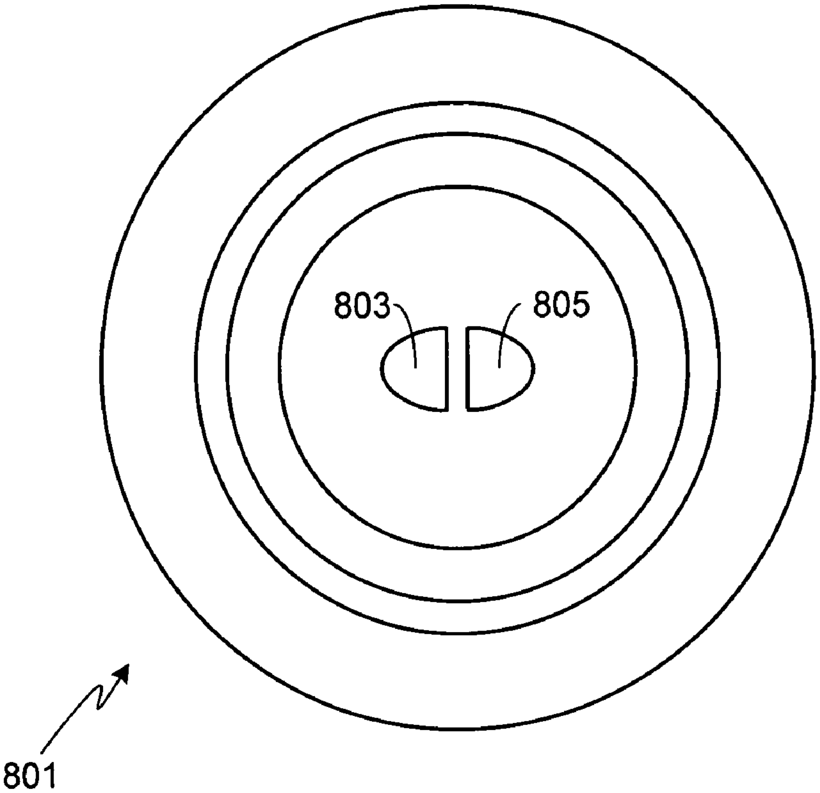
FIG. 8 is an end view of an integrated eartip similar to that shown in FIG. 6 except for the back-to-back “D” shaped sound delivery tubes.
Figure 9:
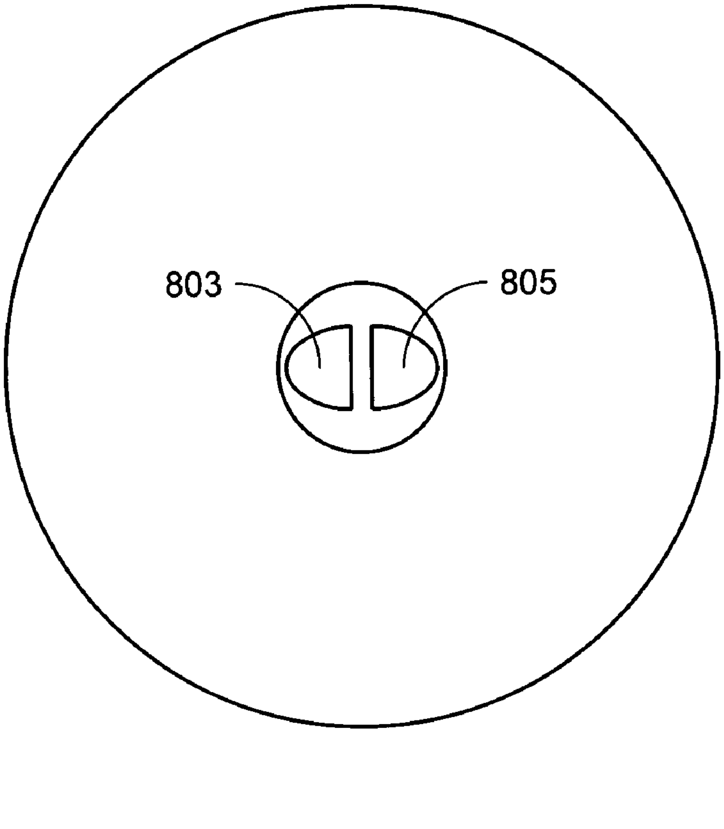
FIG. 9 is an end view of an integrated eartip similar to that shown in FIG. 7 except for the back-to-back “D” shaped sound delivery tubes.

It should be appreciated that the integrated eartip of the present invention can be embodied in a variety of different configurations. For example, the sound delivery tubes of the integrated eartip (e.g., sound delivery tubes 513/515 in FIG. 5) can utilize shapes other than cylindrical. FIGS. 8 and 9 show an input end-view and an output end-view, respectively, of an integrated eartip 801 in which the sound delivery tubes use back-to-back "D" shaped tubes 803/805. Integrated eartip 801 assumes that the output ports of coupling member 503 are also "D" shaped. Clearly other configurations are possible, for example one in which the output ports of coupling member 503, and thus the input ports of the integrated eartip, are cylindrical while the output ports of the integrated eartip are non-cylindrical (e.g., back-to-back "D" shapes). Alternately, the integrated eartip of the invention can utilize a configuration with a single sound delivery tube.

Figure 10:
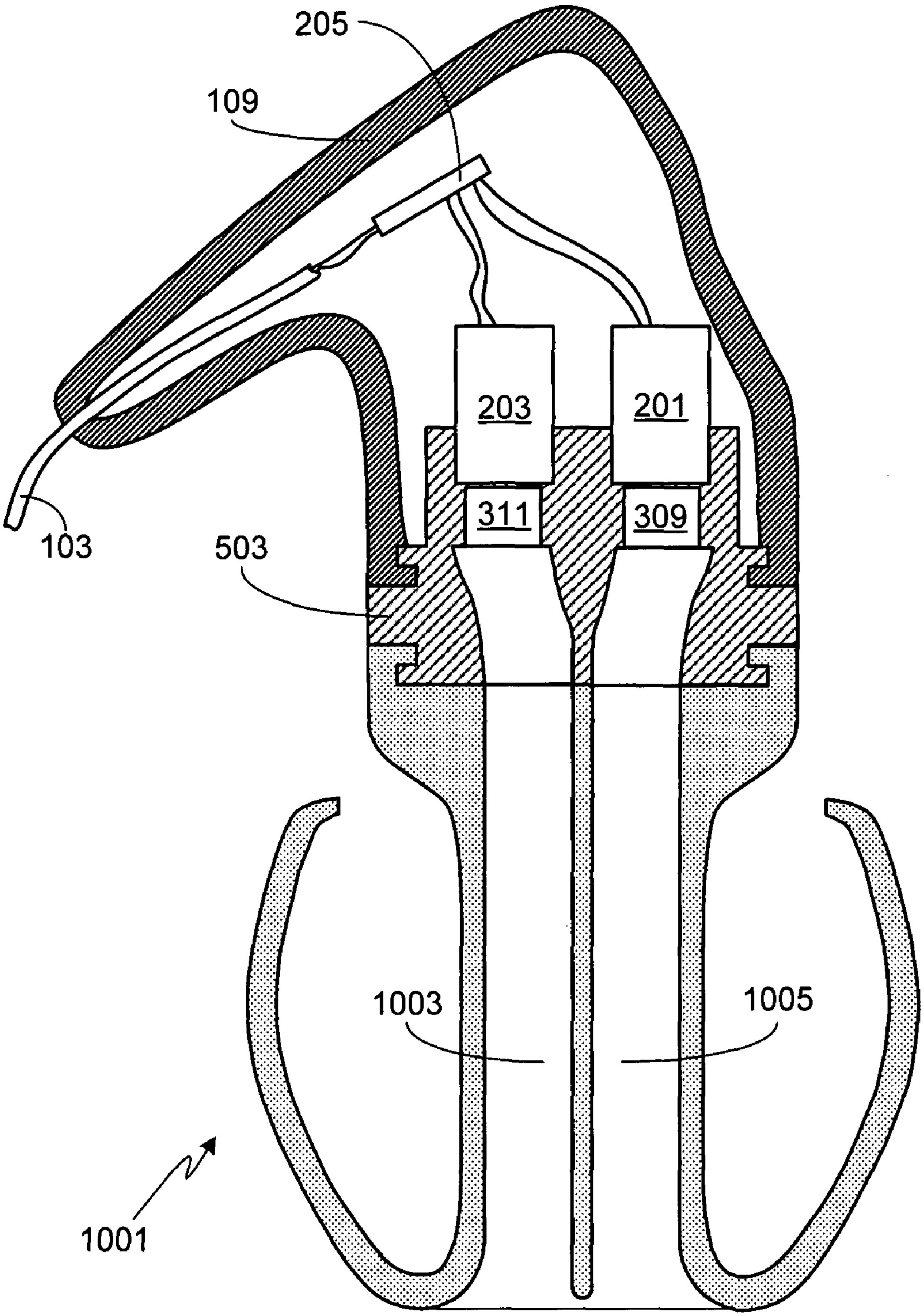
FIG. 10 is a cross-sectional view of an earphone using an integrated eartip similar to that shown in FIG. 5 except for the use of enlarged sound delivery tubes.

Due to the potential for achieving smaller overall diameters, the integrated eartip of the invention can use much larger sound delivery tubes than would be practical with the prior art eartip. FIG. 10 is an illustration of such a configuration. As shown, eartip 1001 includes a pair of large sound delivery tubes 1003/1005. Increasing the bore of the sound delivery tubes allows the earphone to produce higher fidelity audio since the output from the drivers does not have to be squeezed down to the same extent as in a conventional earphone.

Figure 11:
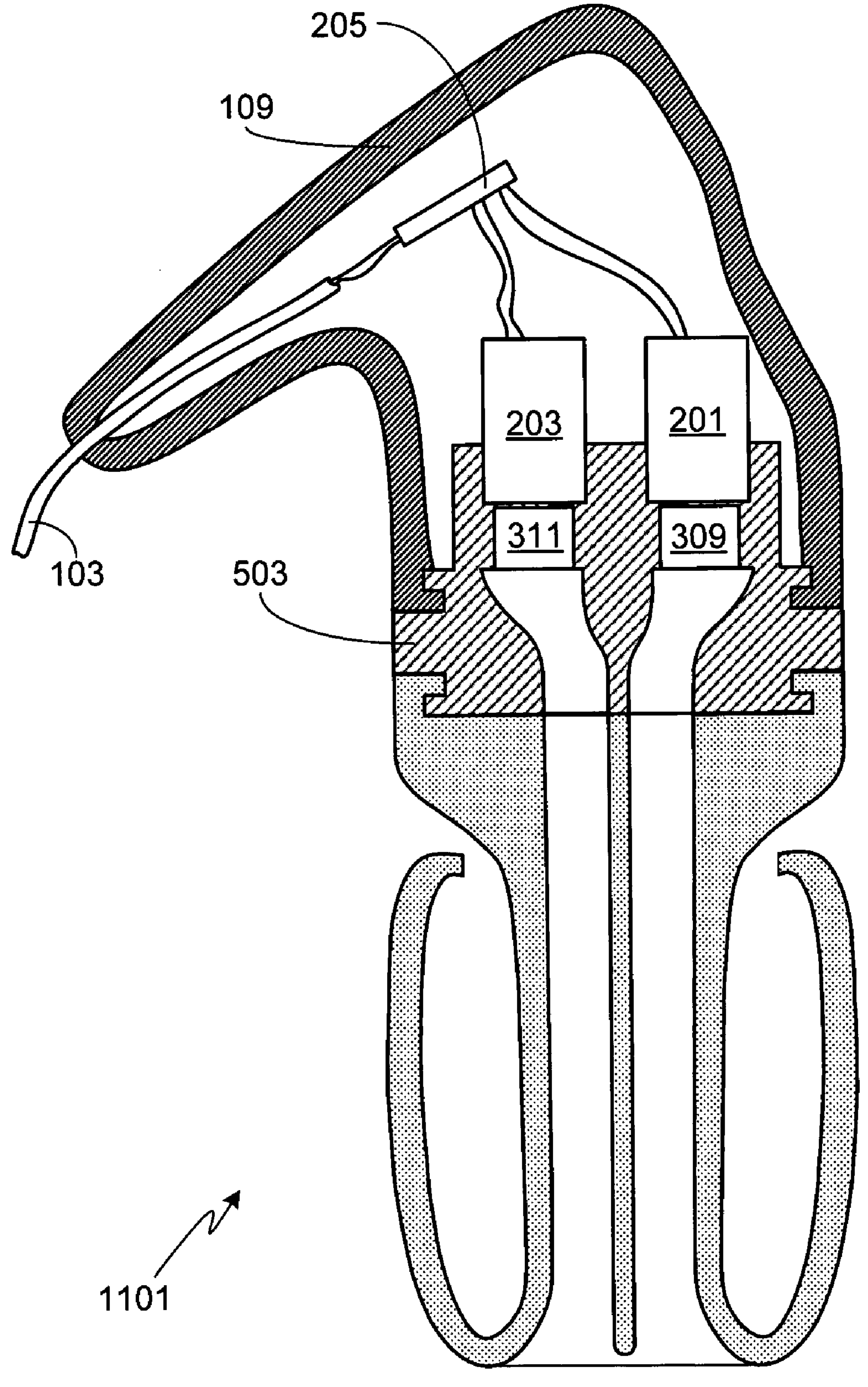
FIG. 11 is a cross-sectional view of an earphone using a small integrated eartip similar to that shown in FIG. 5.

As previously noted, one of the primary advantages of the present invention is that it allows much smaller diameter eartips to be used with the earphone, thus fitting a wider range of users. FIG. 11 is an illustration of one such integrated eartip 1101, for use with the earphone of FIG. 5. It will be appreciated that when compressed, integrated eartip 1101 can fit an extremely small ear canal.

Figure 12:
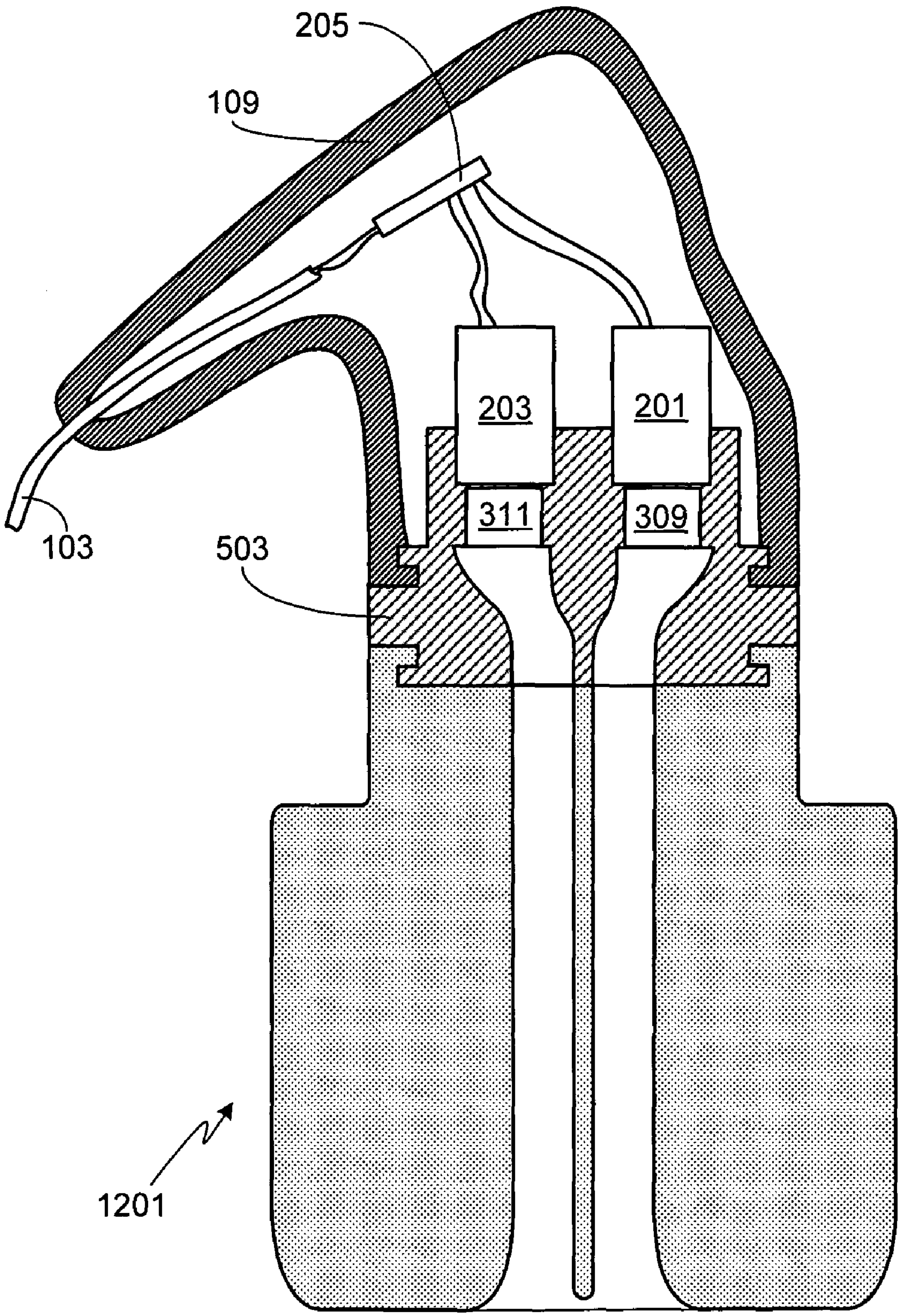
FIG. 12 is a cross-sectional view of an earphone using a solid integrated eartip.
Figure 13:
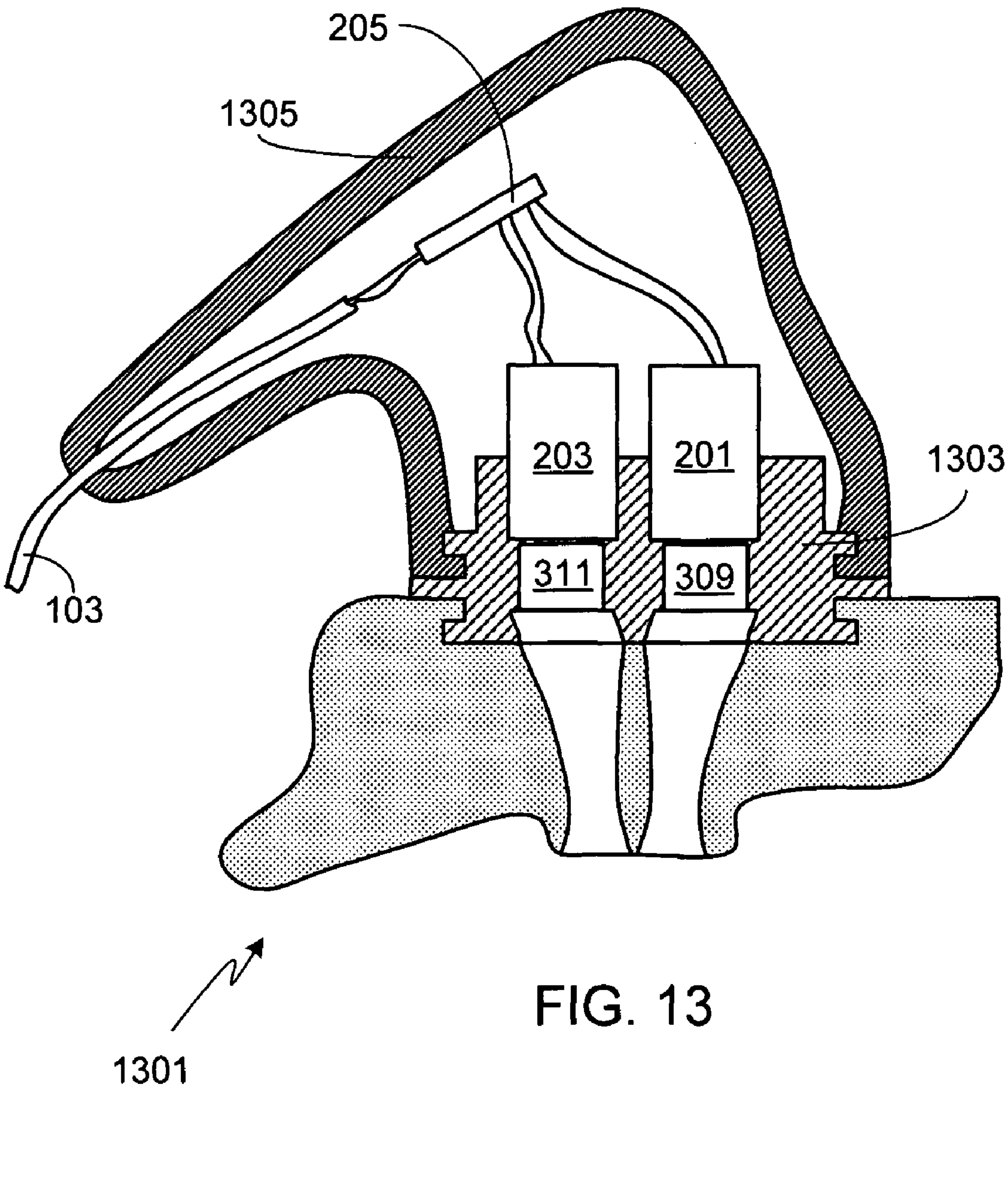
FIG. 13 is a cross-sectional view of an earphone using a molded integrated eartip.

The integrated eartip of the invention is not limited to flanged or finned designs. For example, FIG. 12 illustrates an alternate configuration for an integrated eartip 1201 utilizing a compressible solid material. Another alternate configuration is shown in FIG. 13, integrated eartip 1301 being molded to provide a custom fit for a particular user. As in the previous integrated eartips, integrated eartip 1301 includes sound delivery tubes and is releasably attached to the earphone; releasable attachment providing both easy replacement for maintenance and/or cosmetic reasons as well as simplifying the manufacturing process. In the embodiment shown in FIG. 13, coupling member 1303 and enclosure 1305 are both smaller than in previous embodiments, thus providing further miniaturization of the earphone.

It should be understood that the invention is not limited to earphones utilizing a coupling member such as that shown in FIGS. 5 and 10-13. For example, exemplary embodiments coupling members 503 and 1303 not only provide a means for attaching the integrated eartip and the enclosure, but also include means for securing drivers 201/203 and dampers 309/311 to the assembly. In alternate embodiments, other means such as a separate boot member can be used to secure the drivers and dampers to the assembly. Similarly, the invention is not limited to the use of dampers, to a specific driver type (i.e., armature and/or diaphragm drivers can be used with the invention), or to a specific number of drivers (i.e., single or multiple drivers can be used with the invention). Similarly, the invention is not limited to earphones that utilize an enclosure which is separate from the coupling member, i.e., the functions of the enclosure and the coupling member can be combined into a single component.

Figure 14:
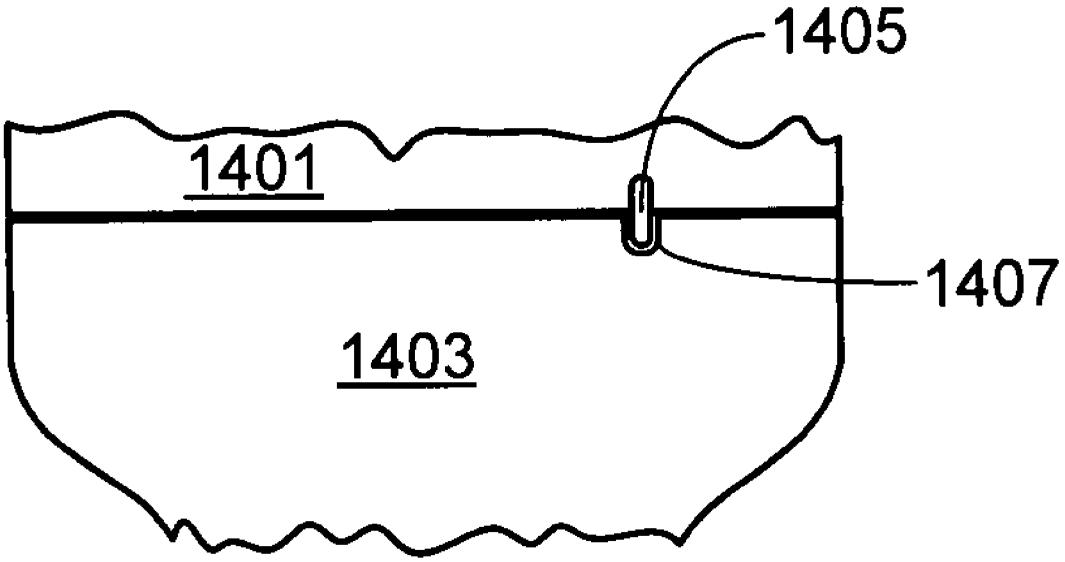
FIG. 14 illustrates a preferred alignment technique to properly align an integrated eartip with a coupling member.

Regardless of the configuration of the coupling member, enclosure, and the integrated eartip, it will be appreciated that the integrated eartip must be properly positioned relative to the coupling member to insure alignment of the output ports of the coupling member and the input ports of the integrated eartip. There are countless techniques for achieving such alignment. In at least one preferred embodiment, the integrated eartip and the coupling member are keyed to insure proper alignment. FIG. 14 is an external view of a portion of a coupling member 1401 and a portion of an integrated eartip 1403. In this embodiment, the coupling member includes a small 'key' 1405 that protrudes from the perimeter of the end portion of the coupling member. A slot 1407 in the end portion of the integrated eartip receives key 1405 when the two components are properly aligned. Alternately, the mating surfaces of the coupling member and the integrated eartip can include a series of irregularly spaced dimples and bumps that are only aligned when the integrated eartip's input ports are properly aligned with the coupling member's output ports. As there are variety of techniques for aligning two components together that are well known by those of skill in the art, further description or examples will not be provided herein.

It will be appreciated that there are many well-known techniques that can be used to fabricate the integrated eartip of the invention. Accordingly, a detailed description of such techniques is not provided herein. Preferred materials for the integrated eartip include both natural (e.g., rubber) and synthetic elastomers (e.g., silicone, neoprene, nitrile rubber, butyl, polyurethane foam, etc.). In at least one preferred embodiment, the integrated eartip is fabricated using a two step insert molding process that allows the material of the inner portion (e.g., surrounding the sound delivery tubes) of the integrated eartip to exhibit more rigid, less compressible characteristics than that of the outer portion, the output portion being compressed during user fitting.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

What is claimed is:

1. An integrated eartip comprising:

a one-piece design, wherein said one-piece design is comprised of a first portion and a second portion, said first portion including at least a first sound delivery tube and a second sound delivery tube and said second portion including a compressible region;

means for releasably attaching said integrated eartip to a coupling member of an earphone, wherein said coupling member includes at least a first acoustic output port acoustically coupled to at least a first driver and at least a second acoustic output port acoustically coupled to at least a second driver, and wherein said first sound delivery tube is aligned with said first acoustic output and said second sound delivery tube is aligned with said second acoustic output when said integrated eartip is attached to said coupling member; and wherein said integrated eartip is comprised of a single material.

2. The integrated eartip of claim 1, wherein a first portion rigidity corresponding to said first portion of said integrated eartip is different from a second portion rigidity corresponding to said second portion of said integrated eartip.

3. The integrated eartip of claim 1, wherein a first portion compressibility corresponding to said first portion of said integrated eartip is different from a second portion compressibility corresponding to said second portion of said integrated eartip.

4. The integrated eartip of claim 1, wherein said single material is selected from the group consisting of natural elastomers and synthetic elastomers.

5. The integrated eartip of claim 1, wherein said releasably attaching means further comprises a channel on an exterior surface of said coupling member and a lip on an inner surface of said integrated eartip, wherein said lip fits within said channel when said integrated eartip is attached to said coupling member.

6. The integrated eartip of claim 1, further comprising a first structure associated with said integrated eartip and a complimentary structure associated with said coupling member, wherein alignment of said complimentary structure with said first structure when said integrated eartip is attached to said coupling member aligns said first sound delivery tube to said first acoustic output and said second sound delivery tube to said second acoustic output.

7. An integrated eartip comprising:

a one-piece design, wherein said one-piece design is comprised of a first portion and a second portion, said first portion including at least a first sound delivery tube and a second sound delivery tube and said second portion including a compressible region;

means for releasably attaching said integrated eartip to a coupling member of an earphone, wherein said releasably attaching means further comprises a first interlocking member on an exterior surface of said coupling member and a second interlocking member on an inner surface of said integrated eartip, wherein said coupling member includes at least a first acoustic output port acoustically coupled to at least a first driver and at least a second acoustic output port acoustically coupled to at least a second driver, and wherein said first sound delivery tube is aligned with said first acoustic output and said second sound delivery tube is aligned with said second acoustic output when said integrated eartip is attached to said coupling member.

8. The integrated eartip of claim 7, wherein a first portion rigidity corresponding to said first portion of said integrated eartip is different from a second portion rigidity corresponding to said second portion of said integrated eartip.

9. The integrated eartip of claim 7, wherein a first portion compressibility corresponding to said first portion of said integrated eartip is different from a second portion compressibility corresponding to said second portion of said integrated eartip.

10. An earphone comprising:

a coupling member;

an earphone enclosure coupled to said coupling member;

means for receiving a signal from an external source;

a first driver disposed within said earphone enclosure and electrically coupled to said receiving means, said first driver having a first acoustic output acoustically coupled to a first output port of said coupling member;

a second driver disposed within said earphone enclosure and electrically coupled to said receiving means, said second driver having a second acoustic output acoustically coupled to a second output port of said coupling member; and an integrated eartip, said integrated eartip comprising:

a one-piece design, wherein said one-piece design is comprised of a first portion and a second portion, said first portion including at least a first sound delivery tube and a second sound delivery tube and said second portion including a compressible region;

means for releasably attaching said integrated eartip to said coupling member, wherein said first sound delivery tube is aligned with said first output port and said second sound delivery tube is aligned with said second output port when said integrated eartip is attached to said coupling member; and wherein said integrated eartip is comprised of a single material.

11. The earphone of claim 10, wherein said receiving means further comprises:

a source input cable attached to said earphone enclosure, wherein said source input cable is coupleable to said external source and receives an electrical signal from said external source, wherein said electrical signal represents a sound to be generated by the earphone, wherein said external source is external to said earphone enclosure, and wherein said external source is selected from the group of sources consisting of music players, mixers and headphone amplifiers; and a circuit contained within said earphone enclosure and electrically coupled to said first driver and said second driver and said source input cable, wherein said electrical signal from said external source is feed through said circuit, said circuit providing a first input signal to said first driver and a second input signal to said second driver.

12. The earphone of claim 10, wherein said coupling member and said earphone enclosure are incorporated into a single component.

13. The earphone of claim 10, wherein a first portion rigidity corresponding to said first portion of said integrated eartip is different from a second portion rigidity corresponding to said second portion of said integrated eartip.

14. The earphone of claim 10, wherein a first portion compressibility corresponding to said first portion of said integrated eartip is different from a second portion compressibility corresponding to said second portion of said integrated eartip.

15. The earphone of claim 10, wherein said single material is selected from the group consisting of natural elastomers and synthetic elastomers.

16. The earphone of claim 10 , wherein said releasably attaching means further comprises a channel on an exterior surface of said coupling member and a lip on an inner surface of said integrated eartip, wherein said lip fits within said channel when said integrated eartip is attached to said coupling member.

17. The earphone of claim 10, further comprising a first structure associated with said integrated eartip and a complimentary structure associated with said coupling member, wherein alignment of said complimentary structure with said first structure when said integrated eartip is attached to said coupling member aligns said first sound delivery tube to said first output port and said second sound delivery tube to said second output port.

18. An earphone comprising:

a coupling member;

an earphone enclosure coupled to said coupling member;

means for receiving a signal from an external source;

a first driver disposed within said earphone enclosure and electrically coupled to said receiving means, said first driver having a first acoustic output acoustically coupled to a first output port of said coupling member;

a second driver disposed within said earphone enclosure and electrically coupled to said receiving means, said second driver having a second acoustic output acoustically coupled to a second output port of said coupling member; and an integrated eartip, said integrated eartip comprising:

a one-piece design, wherein said one-piece design is comprised of a first portion and a second portion, said first portion including at least a first sound delivery tube and a second sound delivery tube and said second portion including a compressible region;

means for releasably attaching said integrated eartip to said coupling member, wherein said releasably attaching means further comprises a first interlocking member on an exterior surface of said coupling member and a second interlocking member on an inner surface of said integrated eartip, wherein said first sound delivery tube is aligned with said first output port and said second sound delivery tube is aligned with said second output port when said integrated eartip is attached to said coupling member.

19. The earphone of claim 18, wherein said receiving means further comprises:

a source input cable attached to said earphone enclosure, wherein said source input cable is coupleable to said external source and receives an electrical signal from said external source, wherein said electrical signal represents a sound to be generated by the earphone, wherein said external source is external to said earphone enclosure, and wherein said external source is selected from the group of sources consisting of music players, mixers and headphone amplifiers; and a circuit contained within said earphone enclosure and electrically coupled to said first driver and said second driver and said source input cable, wherein said electrical signal from said external source is feed through said circuit, said circuit providing a first input signal to said first driver and a second input signal to said second driver.

20. The earphone of claim 18, wherein said coupling member and said earphone enclosure are incorporated into a single component.

21. The earphone of claim 18, wherein a first portion rigidity corresponding to said first portion of said integrated eartip is different from a second portion rigidity corresponding to said second portion of said integrated eartip.

22. The earphone of claim 18, wherein a first portion compressibility corresponding to said first portion of said integrated eartip is different from a second portion compressibility corresponding to said second portion of said integrated eartip.

* * * * *